(12) United States Patent
Canaud et al.

(10) Patent No.: US 12,186,177 B2
(45) Date of Patent: Jan. 7, 2025

(54) STENT-TYPE AORTIC IMPLANT AND ASSEMBLY FORMED BY TWO SUCH IMPLANTS

(71) Applicants: Ludovic Canaud, Montpellier (FR); Thomas Gandet, Montpellier (FR)

(72) Inventors: Ludovic Canaud, Montpellier (FR); Thomas Gandet, Montpellier (FR)

(*) Notice: Subject to any disclaimer, the term of this patent is extended or adjusted under 35 U.S.C. 154(b) by 756 days.

(21) Appl. No.: 17/284,720

(22) PCT Filed: Oct. 9, 2019

(86) PCT No.: PCT/EP2019/077390
§ 371 (c)(1),
(2) Date: Apr. 12, 2021

(87) PCT Pub. No.: WO2020/074598
PCT Pub. Date: Apr. 16, 2020

(65) Prior Publication Data
US 2021/0369439 A1    Dec. 2, 2021

(30) Foreign Application Priority Data

Oct. 12, 2018  (FR) ...................................... 1871165

(51) Int. Cl.
*A61F 2/07* (2013.01)
*A61F 2/06* (2013.01)
*A61F 2/856* (2013.01)

(52) U.S. Cl.
CPC ................ *A61F 2/07* (2013.01); *A61F 2/856* (2013.01); *A61F 2002/061* (2013.01); *A61F 2250/0098* (2013.01)

(58) Field of Classification Search
CPC ...... A61F 2/07; A61F 2/856; A61F 2002/061; A61F 2250/0098; A61F 2/072;
(Continued)

(56) References Cited

U.S. PATENT DOCUMENTS

2003/0135257 A1    7/2003  Taheri
2005/0154442 A1    7/2005  Eidenschink
(Continued)

FOREIGN PATENT DOCUMENTS

CN    103747761    4/2014
CN    104066401    9/2014
(Continued)

*Primary Examiner* — Jerrah Edwards
*Assistant Examiner* — Maximilian Tobias Spencer
(74) *Attorney, Agent, or Firm* — Defillo & Associates, Inc; Evelyn A. Defillo

(57) ABSTRACT

The implant includes an aortic portion and a branch, which is intended to be placed in a first of the three arteries that lead into the aortic arch. The aortic portion and branch are formed by two separate sub-assemblies which are capable of being mounted together; the aortic portion has a first opening capable of receiving the branch and a second opening arranged such that it is located substantially opposite the outlets of the other two arteries when the first opening is located opposite the outlet of the left subclavian artery. The second opening has a specific shape such that the edges of the membrane that define it follow the segments of the underlying annuli, which are in a broken line.

13 Claims, 4 Drawing Sheets

(58) Field of Classification Search
CPC .. A61F 2/075; A61F 2/954; A61F 2230/0054; A61F 2250/006–0065
See application file for complete search history.

(56) References Cited

U.S. PATENT DOCUMENTS

| | | | |
|---|---|---|---|
| 2010/0114294 A1* | 5/2010 | Rasmussen | A61F 2/07 623/1.15 |
| 2012/0136431 A1 | 5/2012 | Chen | |
| 2013/0079870 A1 | 3/2013 | Roeder et al. | |
| 2014/0296963 A1 | 10/2014 | Akingba | |
| 2016/0030209 A1* | 2/2016 | Shalev | A61F 2/07 623/1.35 |
| 2016/0067067 A1 | 3/2016 | Roselli | |
| 2016/0262880 A1 | 9/2016 | Li et al. | |
| 2018/0116783 A1* | 5/2018 | Kratzberg | A61F 2/07 |
| 2018/0153677 A1 | 6/2018 | Perkins | |
| 2018/0200089 A1 | 7/2018 | Eller | |
| 2019/0388214 A1* | 12/2019 | Silverman | A61F 2/07 |

FOREIGN PATENT DOCUMENTS

| | | |
|---|---|---|
| CN | 204428217 | 7/2015 |
| EP | 3017790 | 5/2016 |
| FR | 2979229 | 3/2013 |
| FR | 2995206 | 3/2014 |
| WO | WO2007028086 | 3/2007 |
| WO | WO2010030370 | 3/2010 |
| WO | WO2014141232 | 9/2014 |

* cited by examiner

STENT-TYPE AORTIC IMPLANT AND ASSEMBLY FORMED BY TWO SUCH IMPLANTS

CROSS REFERENCE TO RELATED APPLICATION

This application is a national stage entry of PCT/EP2019/077390 filed Oct. 9, 2019, under the International Convention and claiming priority over French Patent Application No. 1871165 filed Oct. 12, 2018.

FIELD OF THE INVENTION

This invention relates to a stent-type aortic implant.

As we know, the aorta makes a 180° curve after leaving the heart, and we see the aortic arch, i.e. the top of the curved portion of the aorta, the "ascending" aorta, i.e. the part of this curved portion located between the heart and the arch, and the "descending" aorta, i.e. the part of this curved portion located between the arch and the end of the curved portion. The brachiocephalic, left common carotid and left subclavian arteries come directly off the aortic arch and supply blood to the brain.

Several types of lesion may affect the aortic arch: degenerative aneurysms, which consist in an increase in the diameter of the aorta of at least twice the normal diameter, aortic dissections, which consist in a tear in the lining of the aorta depending on the thickness of this lining, traumatic ruptures of the aortic arch, aortic ulcers, which are perforations due to the presence of atheroma. The risk generated by these types of lesion is that of a rupture of the aortic arch resulting in internal hemorrhage and inevitable death. All these lesions represent a surgical indication if the diameter of the aorta exceeds 5.5 cm or if they are symptomatic.

BACKGROUND OF THE INVENTION

It is known to treat these types of lesion through the use of a stent-type aortic implant, comprising a deployable wire frame and a membrane covering this frame. An implant currently used for this treatment is in fact an implant designed for the treatment of conditions of the descending aorta or of the thoracic aorta (beyond the descending aorta), of minimum length ten centimeters. The implant, placed in contracted state inside a sheath, is inserted by endovascular route up to the aortic arch and is deployed so as to cover the aortic lesion. The above-mentioned arteries, whose outlets in the aorta will be covered by the implant, must first be diverted: these diversions consist of bypasses, which are produced by opening the thoracic cage and partially stopping the circulation in the aorta; these operations are long and complex, and the need for their implementation is a major disadvantage of this implant.

Other customized implants have been developed. This type of implant has an aortic portion to which two branches are connected; these branches are intended to be placed in two of the above-mentioned arteries with cerebral destination: the blood flow in the last of these three arteries is maintained by bypass surgery. This technique allows almost fully endovascular treatment: it nevertheless has many disadvantages: firstly, the need for a bypass to maintain the perfusion of one of the three above-mentioned arteries since the aortic implant only allows the use of two branches; secondly, the branches are inserted through the outlets of two of the cerebral arteries, which involves temporarily stopping the cerebral perfusion and handling these arteries, resulting in a high risk of ischemic stroke; thirdly, the delay required to manufacture this type of customized implant is a major constraint, preventing the use of this type of implant in an emergency situation or for patients who are asymptomatic but suffer from a large aortic lesion with a high risk of rupture.

In addition, the publication of patent application No. EP 3 017 790 A2 describes an implant whose characteristics are defined by the pre-characterizing part of the appended claim 1. The implant according to this previous document provides only a very partial remedy to the above-mentioned disadvantages. Indeed, it cannot be used to treat a certain number of conditions likely to affect the ascending portion of the aorta and the proximal portion of the aortic arch. In addition, the implant according to this previous document is specifically intended to be inserted anterogradely from the brachiocephalic artery, which explains why it has a proximal notch; this notch does not provide the implant with the tightness required at the outlets of the brachiocephalic and left common carotid arteries and does not allow the perfusion of the brachiocephalic artery and of the left carotid artery under the best conditions. The anchoring of the implant could also be improved. In addition, the position of the aortic portion of the implant relative to the left subclavian artery is inaccurate.

OBJECT AND SUMMARY OF THE INVENTION

This invention aims to overcome all these disadvantages.

The implant concerned comprises, in a known manner, an aortic portion and a branch intended to be placed in the left subclavian artery; said aortic portion comprises a deployable wire frame and a membrane covering this frame;

said deployable frame includes annuli independent of each other and connected to each other only by means of the membrane, each one being formed by a broken line-shaped wire, each annulus thus having straight segments separated by bends, two consecutive segments and a bend which extends between these segments defining a V-shaped structure; the frame comprises first, second, third and fourth annuli counted from the proximal end of the aortic portion;

said aortic portion and said branch are formed by two separate sub-assemblies that can be assembled to each other;

said branch is formed by a deployable frame adapted, in a contracted state, to be engaged in the left subclavian artery and adapted, in an expanded state, to press against the lining of this artery;

said aortic portion comprises a first opening created through said membrane, dimensioned so as to have an area at least equal, or less than, the transverse cross-section of said branch in its deployed state in the left subclavian artery; said aortic portion further comprises a second opening created through said membrane, arranged relative to said first opening, and dimensioned so as to be located substantially opposite the outlet of the left common carotid artery when said first opening is located substantially opposite the outlet of the left subclavian artery.

According to the invention, the centre of said first opening is located on the axis of symmetry of a first V-shaped structure formed by said third annulus, the two segments of this first V-shaped structure diverging towards the proximal end of said aortic portion; the first opening is defined by an edge provided with a reinforcement which extends over the entire periphery of this first opening;

said second opening comprises a proximal portion arranged above a second V-shaped structure formed by said second annulus, the two segments of this second structure diverging towards the proximal end of the aortic portion and being located on said axis of symmetry; lengthwise, said second opening extends between:

a transverse proximal edge located at the distal bend formed by a third V-shaped structure, located on said axis of symmetry, of said first annulus;

first lateral edges, diverging in the distal direction, which extend along the segments consecutive to the segments forming said second V-shaped structure;

second lateral edges, converging in the distal direction, which extend along the segments of said first V-shaped structure; and the distal bend formed by said first V-shaped structure;

said first to fourth annuli are consecutive to each other, or immediately consecutive to each other, said second opening being dimensioned so that it is located substantially opposite the outlets of the brachiocephalic and left common carotid arteries after placing the implant;

the edges of the membrane which define said second opening being successively connected, from the proximal side and towards the distal side of the aortic portion, to the distal bend formed by said third V-shaped structure, to said segments consecutive to the segments forming said second V-shaped structure, to said segments forming said first V-shaped structure and to said distal bend formed by this first V-shaped structure.

In practice, said aortic portion, in its contracted state, is engaged in the aorta and is positioned such that one or more radio-opaque markers present on the aortic portion are positioned substantially opposite the outlet of said first artery; the aortic portion is then partially deployed in the aorta up to its portion which comprises said first opening; said branch is, while it is in its contracted state, engaged in the left subclavian artery then through said first opening and is then deployed in this first opening then in the left subclavian artery, this deployment allowing this branch to be connected to the aortic portion of the implant and to this artery; the reinforcement provided on the edge of said membrane which defines said first opening allows this edge to withstand the force resulting from the deployment of said branch with no risk of tearing the membrane; the implant is thus positioned both longitudinally and angularly in the aorta. The remainder of said aortic portion is then deployed to finish placing the implant. Said second opening is thus perfectly positioned opposite the outlets of the two arteries other than the left subclavian artery, and the aortic portion is perfectly pressed around these outlets due to the presence of said segments of the V-shaped structures along most of the edges of the membrane which define this second opening. Perfusion of the brachiocephalic artery and of the left carotid artery can therefore be performed under the best conditions. In addition, said second V-shaped structure, free from any membrane, is deployed in the brachiocephalic artery and improves the anchoring of the implant and the conformability of said second opening. In addition, since said aortic portion forms said second opening, it therefore comprises a proximal portion that can extend not only at the proximal portion of the arch of the aorta but also in the ascending portion of this aorta, which means that the implant according to the invention can treat pathologies developing in these locations.

The implant according to the invention is thus designed so as to comprise an aortic portion and a branch forming two separate sub-assemblies, and to comprise a first opening of dimension adapted to connect said branch to said aortic portion when this branch is in its deployed state. This connection allows accurate positioning of said aortic portion in the aorta and therefore positioning of said second opening substantially opposite the outlets of the two arteries other than the left subclavian artery. Once in position therefore, the implant does not cover any of the outlets of the three above-mentioned arteries and consequently does not require the implementation of one or more bypasses. In addition, the positioning of this implant does not involve any handling of the left subclavian artery or of one or both of said two other arteries, thereby eliminating the risk of an ischemic stroke. Furthermore, this implant can be manufactured relatively quickly, so there is no major constraint in this respect.

Preferably, said reinforcement is radio-opaque and flexible, and said first opening is located near the distal bend of said first V-shaped structure formed by said third annulus.

Said first opening is therefore located between the segments of the adjacent V-shaped structure of the fourth annulus; in the contracted state of the deployable frame, these segments are close together, contracting the portion of the membrane extending between them and thus, bringing the reinforcement of said first opening into a contracted state; in this contracted state, this reinforcement forms an elongated mark on a medical imaging image and therefore represents a reliable way of indicating the orientation of said aortic portion, in order to accurately define the location of the first opening along said aortic portion.

Preferably, the distal bends of one of said first to third annuli are located at a distance of 0 to 10 mm from a plane transverse to the aortic portion passing through the proximal bends of the distally adjacent annulus.

The diameter of said first to fourth annuli, in the deployed state could be equal to that of the membrane in the deployed state; preferably, however, the diameter of these annuli, in the deployed state, is greater than that of the membrane in the deployed state.

The fabric formed by the membrane is thus stretched at the edges which define said second opening and a puckered effect is therefore avoided. The membrane is firmly pressed around the outlets of the two above-mentioned arteries and leaks are avoided.

Preferably, the diameter of the annuli in the deployed state is 1 to 30% greater than that of the membrane in the deployed state, and preferably about 20% greater than this diameter.

Said branch could be connected to said aortic portion by simply pressing this branch against said reinforcement defining said first opening; preferably, however, the end of said branch, intended to be engaged through said first opening has, in the deployed state of said branch, a collar or a flared portion of diameter greater than that of said first opening, this collar or this flared portion thus being able to press against said aortic portion of the implant, on the inner side of the latter.

A reliable connection between said branch and said aortic portion is thus obtained.

The diameter of said first opening may range from 5 to 11 mm, and is preferably equal to 8 mm.

The dimension of said second opening in the longitudinal direction of said aortic portion may range from 20 to 40 mm and in the circumferential direction of this aortic portion from 20 to 40 mm.

Said aortic portion advantageously comprises one or more radio-opaque markers located near said second opening, arranged so as to display the plane of this second opening on a medical imaging image.

These markers can therefore be used to also display the position of this second opening.

The invention further relates to an assembly formed by two stent-type aortic implants as mentioned above, this assembly comprising:

a first implant in which the edge of said first opening turned towards the adjacent edge of said second opening is located at a distance from this adjacent edge ranging from 4 to 8 mm, preferably equal to 5 mm; and a second implant in which the edge of said first opening turned towards the adjacent edge of said second opening is located at a distance from this adjacent edge ranging from 8 to 12 mm, preferably equal to 10 mm.

It appears that the first implant can treat about 80% of patients; the second implant can treat 20% of the remaining patients.

BRIEF DESCRIPTION OF THE DRAWINGS

The invention will be easier to understand and other characteristics and advantages will appear on reading the following description, with reference to the accompanying schematic drawing representing, as non-limiting example, a preferred embodiment of the implant concerned.

MORE DETAILED DESCRIPTION

Figure 3:
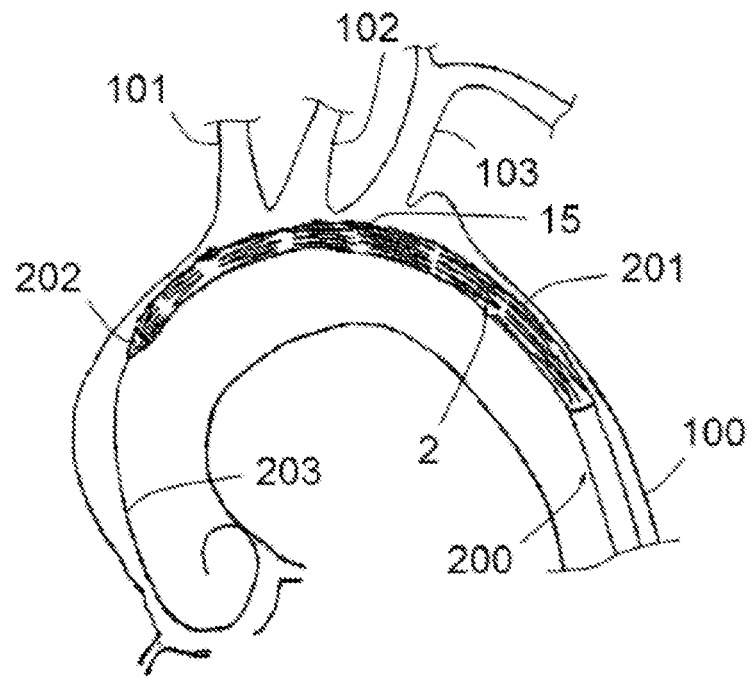
FIG. 3 is a cross-sectional view of an aorta and of said aortic portion in a contracted state, during a first step of positioning this aortic portion in this aorta.
Figure 4:
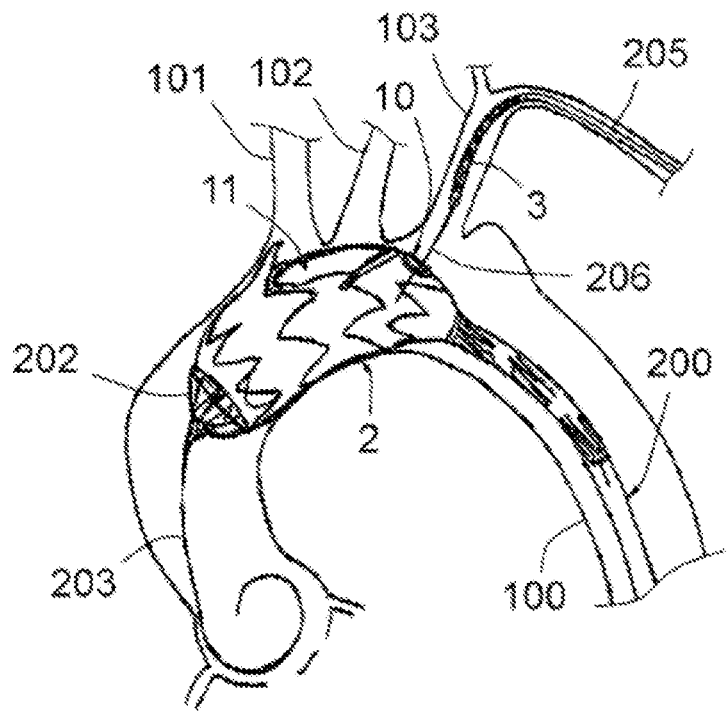
FIG. 4 is view similar to FIG. 3, with said aortic portion being partially deployed; a lateral branch consisting of a stent, which forms the implant with said aortic portion, is engaged, in a contracted state, through the left subclavian artery.
Figure 5:
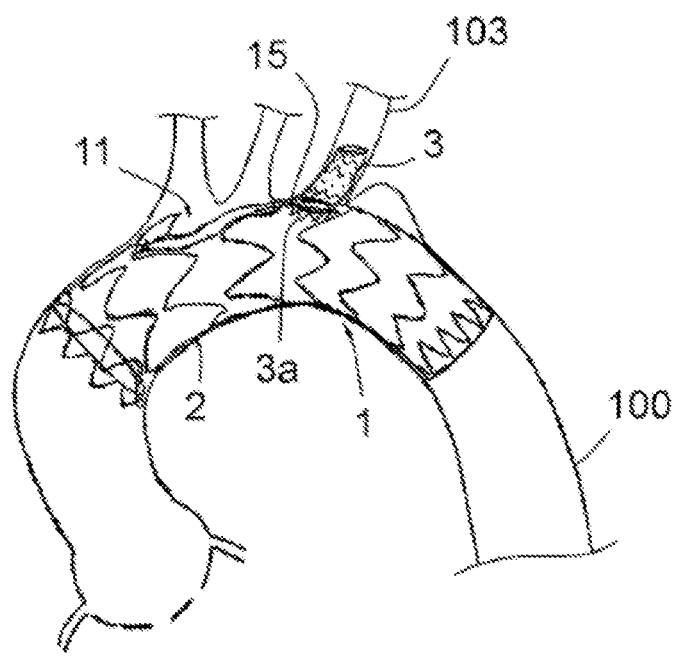
FIG. 5 is a view similar to FIG. 4 of the implant once in position, said aortic portion and said branch being fully deployed.

FIGS. 3 to 5 are highly schematic cross-sectional views in a front plane of an aorta 100 and the brachiocephalic 101, left common carotid 102 and left subclavian 103 arteries that lead into the aorta 100 and supply blood to the brain.

Figure 1:
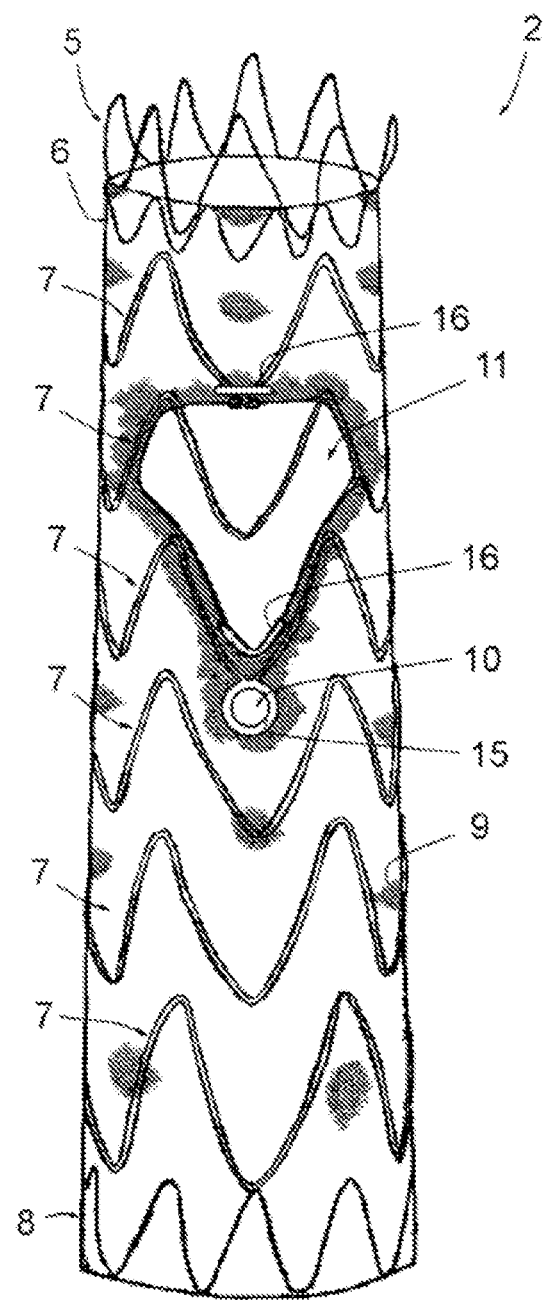
FIG. 1 is a side view, along a first direction, of an aortic portion of this implant.
Figure 2:
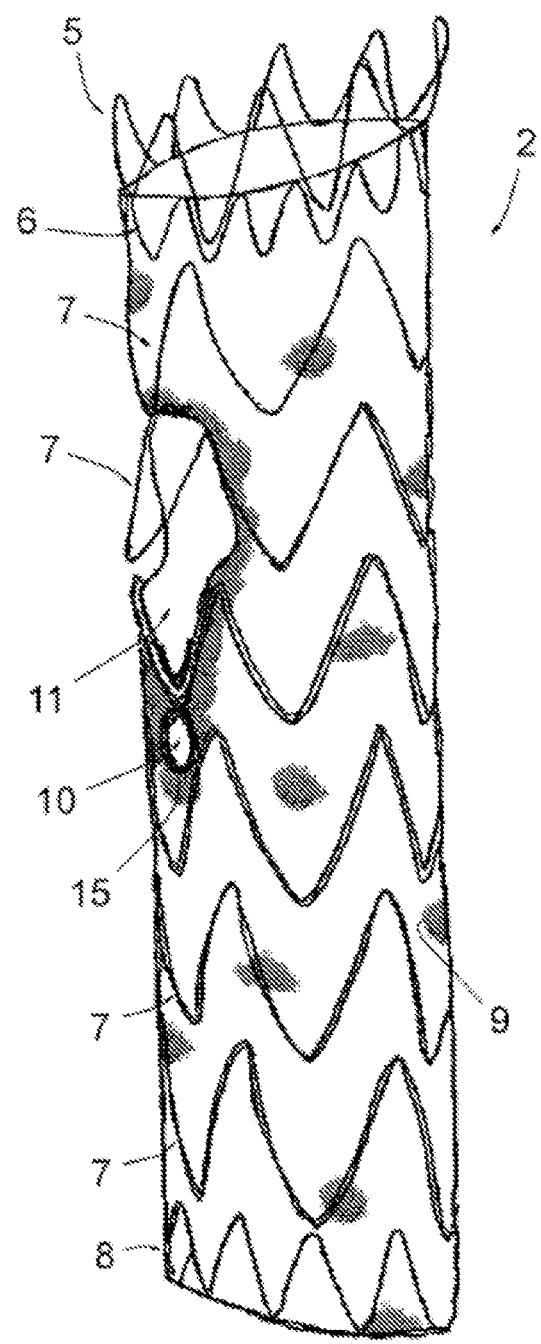
FIG. 2 is a side view of said aortic portion, along a second direction, substantially perpendicular to said first direction.

FIG. 5 shows the stent-type aortic implant 1 according to the invention, which is formed by the aortic portion 2 shown on FIGS. 1 and 2 and by the branch 3 deployed in the left subclavian artery 103. This aortic portion 2 and this branch 3 form two separate sub-assemblies that can be assembled to each other.

As shown in particular on FIGS. 1 and 2, the aortic portion 2 is of the stent type, i.e. it comprises a deployable wire frame 5, 6, 7, 8 and a membrane 9 covering this frame.

For clarity purposes, the membrane 9 is only partially represented on the drawing; it is nevertheless shown substantially completely around two of its openings 10 and 11, so that these two openings are clearly visible. To display the various elements 5, 6, 7, 8 forming said frame, the membrane 9 is shown fictitiously as being transparent but, still for clarity purposes, the parts of these elements 5, 6, 7, 8 which are located in half of the circumference of the aortic portion 2 and visible in the background on the figures are not shown.

In the example shown, the frame 5, 6, 7, 8 is formed, from its proximal end towards its distal end, by a series of annuli 5 to 8, each one being formed by a broken line-shaped wire. In the usual way, the proximal-distal direction must be considered in the direction of blood flow through the aorta 100.

This well-known broken line-shaped structure allows the aortic portion 2 to take up a contracted state shown on FIG. 3 when the aortic portion 2 is placed in a sheath 201 included in the catheter 200 for the insertion and positioning of this aortic portion 2; this broken line-shaped structure also allows the aortic portion 2 to take up, by shape memory or by deployment using a balloon, an expanded state shown on FIG. 5, in which the aortic portion 2 is in contact with the lining of the aorta 100. In addition, the annuli 5 to 8 are independent of each other and are connected to each other only by means of the membrane 9, such that the aortic portion 2 is sufficiently deformable transversally to follow the curve of the aorta 100.

The frame 5, 6, 7, 8 can in particular be made of a nickel-titanium alloy, and the membrane 9 can in particular be made of woven polyester or expanded polytetrafluoroethylene.

In the example shown, an end proximal annulus 5 comprises, between the bends formed by the broken line defined by this annulus, segments of lengths greater than those of the similar segments comprised in a second end proximal annulus 6; the lengths of these segments of annulus 5 are shorter than those of the segments of annuli 7. The frame is completed by an end distal annulus 8 whose segments have substantially the same lengths as those of the segments of the proximal annulus 6, or are slightly longer.

The annuli 7 are referred to below as the "central" or "body" annuli of the aortic portion to distinguish them from the end annuli 5, 6 and 8.

Being only very partially covered by the membrane 9, the annulus 5 can hold the proximal end of the aortic portion 2 when positioning this aortic portion 2, by means of a deployable proximal holding part 202, carried by a guide wire 203 included in the catheter 200 used to insert the aortic portion 2 in the aorta 100. Such an introduction catheter is traditional and well-known, and is therefore not particularly detailed. Having no membrane 9 around it, the annulus 5 also increases the anchoring of the proximal end of the aortic portion 2 to the aorta 100; the inverted V-shaped structures which it forms can be slightly deflected radially towards the outside, as shown on FIG. 2, to improve the anchoring of this annulus 5 to the lining of the aorta 100.

The annulus 6 holds the proximal end of the membrane 9 in the deployment position.

The central annuli 7 are used to deploy the membrane 9 and to hold it against the lining of the aorta 100; they contribute to holding the aortic portion 2 in the aorta 100 in the longitudinal direction. Each of these central annuli 7 consists of a broken line-shaped wire, and therefore comprises straight segments separated by bends; two consecutive segments and a bend extending between these segments define a structure referred to below as "V-shaped structure". Each annulus 7 forms five or six V-shaped structures. To differentiate between these central annuli 7 in the description given below, they will be referred to respectively as first, second, third and fourth annuli, and so on, from the proximal end of the aortic portion 2 towards the distal end of this portion, therefore from the upper parts of FIGS. 1 and 2 going down towards the lower part of these figures.

The annuli 7 are consecutive to each other, or immediately consecutive to each other, since the distal bends of one of said first to third annuli 7 are located at a distance from a plane transverse to the aortic portion 2 separating these distal bends from the proximal bends of the adjacent annulus 7, which is equal to 0 mm in the example shown, or which may otherwise range from 1 to 10 mm.

The annulus 8 holds the distal end of the membrane 9 in the deployment position.

The two openings 10 and 11 are formed on one side of the aortic portion 2, through the membrane 9, one after the other but separated from each other.

The opening 10 is circular and is defined by a peripheral reinforcement 15 stitched to the membrane 9. This reinforcement 15 reinforces the entire periphery of the opening 10 while being flexible, i.e. not preventing a contraction of the opening 10 when the membrane is contracted radially, in the contracted state of the aortic portion 2. The reinforcement 15 further comprises a radio-opaque product so that it can be seen on a medical imaging image.

The inner diameter of the opening 10 is 8 mm, and is slightly less than the transverse cross-section of the branch 3 in its deployed state in the artery 103.

In the example show, the opening 10 is located near the distal bend of a first V-shaped structure formed by the third annulus 7 from the proximal end of the aortic portion 2, the two segments of this V-shaped structure diverging towards the proximal end of this aortic portion 2; the centre of the opening 10 is located substantially on the axis of symmetry of this first V-shaped structure; this centre is located substantially half-way along the membrane 9.

In the example shown, the opening 11 is formed above a second V-shaped structure formed by the second annulus 7, from the proximal end of the aortic portion 2, the two segments of this second structure diverging towards the proximal end of the aortic portion 2 and being located on said axis of symmetry. Lengthwise, the opening 11 extends between:
- a transverse proximal edge located at the distal bend formed by a third V-shaped structure formed, on said axis of symmetry, by the first annulus 7;
- first lateral edges, diverging in the distal direction, which extend between the segments located each side of the segments forming said second V-shaped structure, and therefore consecutive to these segments on the circumference of said second annulus 7;
- second lateral edges, converging in the distal direction, which extend along the segments of said first V-shaped structure of the third annulus 7; and
- the distal bend formed by said first V-shaped structure.

The opening 11 is therefore "pear-shaped", its wider part being directed towards the proximal side and its tip being directed towards the distal side.

The edges of the membrane 9 which define said second opening 11 are connected, from the proximal side and towards the distal side of the aortic portion 2, to the distal bend formed by said third V-shaped structure, to said segments outside said second V-shaped structure, to said segments of said first V-shaped structure and to said distal bend formed by this first V-shaped structure. These edges of the membrane 9 are therefore perfectly connected to the annuli 7 concerned and are therefore perfectly reinforced and held by these annuli.

The membrane 9 further comprises inserts 16 made of radio-opaque material, including one, in the example shown, which is attached to the distal bend of said third V-shaped structure and the other is attached to the distal bend of said first V-shaped structure. These inserts 16 show the position of the opening 11 on a medical imaging image.

The branch 3 is of the stent type, being formed by a deployable frame. As shown on FIG. 4, this branch 3 is adapted, in a contracted state, to be engaged in the left subclavian artery 103, by means of a catheter 205; as shown on FIG. 5, the branch 3 is adapted, in an expanded state, to be engaged through the opening 10 and to press against the lining of the left subclavian artery 103.

The end of the branch 3 intended to be engaged through the opening 10 has, in the deployed state of the branch 3, a collar or a flared portion 3a of diameter greater than that of the opening 10. This collar or this flared portion 3a is thus adapted to press against the membrane 9, at the inner side of the membrane and at the annulus 15, as shown on FIG. 5.

FIGS. 3 to 5 illustrate three successive steps of the positioning of the implant 1 formed by the aortic portion 2 and the branch 3.

In practice, the aortic portion 2, held in its contracted state by the sheath 201, is engaged in the aorta 100 by endovascular route, being guided by the guide wire 203; a shown on FIG. 3, it is positioned so that the reinforcement 15 is placed substantially opposite the outlet of the left subclavian artery 103. This reinforcement 15, as shown in the contracted state of the membrane by medical imaging, forms an elongated radio-opaque mark representing a reliable way of indicating the orientation of said aortic portion 2, in order to accurately define the location of the opening 10 along this aortic portion 2.

The aortic portion 2 is then partially deployed in the aorta 10 up to its portion which comprises the opening 10, which positions the opening 11 substantially opposite the outlets of the brachiocephalic 101 and left common carotid 102 arteries. Since this aortic portion forms this opening 11, it therefore comprises a proximal portion that can extend not only at the proximal portion of the arch of the aorta but also in the ascending portion of this aorta, which means that the implant can treat pathologies developing in these locations.

In this position, the opening 11 is perfectly positioned opposite the outlets of the two arteries 101, 102, and the aortic portion 2 is perfectly pressed around these outlets due to the presence of said segments of the V-shaped structures along most of the edges of the membrane 9 which define this opening 11. Perfusion of the brachiocephalic artery and of the left carotid artery can therefore be performed under the best conditions. In addition, said second V-shaped structure, free from any membrane, is deployed in the brachiocephalic artery and improves the anchoring of the implant and the conformability of the opening 11.

A guide wire 206 is then inserted in the left subclavian artery 103 then through the opening 10, up to the inside of the aortic portion 2, then the catheter 205, containing the branch 3 held in the contracted state by a sheath, is used to bring, by sliding on this guide wire 206, the branch 3 through this artery 103, as shown on FIG. 4.

This branch 3 is moved forward until its proximal portion is engaged through the opening 10, then the sheath of the catheter 205 is moved backward to start deploying the branch 3. The collar or flared portion 3a of the end of the branch 3 is thus deployed inside the aortic portion 2 and presses against the inner side of the membrane 9, at the reinforcement 15, thus connecting the branch 3 to the aortic portion 2. The reinforcement 15 allows the membrane 9 to withstand the force resulting from the deployment of the branch 3, with no risk of tearing this membrane.

The deployment of the branch 3 continues until this branch 3 presses against the lining of the left subclavian artery 103, then the catheter 205 is removed.

The implant 1 is thus positioned both longitudinally and angularly in the aorta 100, by deployment of the branch 3 in the artery 103 and by the connection of this branch 3 to the aortic portion 2, and is perfectly held in this position.

The proximal annulus 5 is then released by the part 202 and the rest of the aortic portion 2 is deployed in the descending aorta, as shown on FIG. 5, with no risk of moving the implant 1.

The invention thus provides a stent-type aortic implant which overcomes the disadvantages of similar implants of the prior art, since it can be accurately positioned in the aorta, and it can be used to accurately position the openings or windows through its lining opposite the outlets of the brachiocephalic, left common carotid and left subclavian arteries, thereby removing the need for bypasses; the positioning of this implant does not involve any handling of said arteries, thereby eliminating the risk of an ischemic stroke; furthermore, this implant can be manufactured relatively quickly, so there is no major constraint in this respect.

What is claimed is:

1. A stent-type aortic implant comprising:
   an aortic portion and a branch intended to be placed in a left subclavian artery; said aortic portion is one-piece and comprises a deployable wire frame and a membrane covering the frame; wherein:
   said deployable frame includes annuli independent of each other and connected to each other only by the membrane, each one being formed by a broken line-shaped wire, each annulus having straight segments separated by bends, two consecutive segments and a bend which extends between the segments defining a V-shaped structure; the frame comprises a first, a second, a third and a fourth annuli counted from a proximal end of the aortic portion, said proximal end of the aortic portion is configured to be positioned in the ascending aorta;
   said aortic portion and said branch are formed by two separate sub-assemblies assembled to each other;
   said branch is formed by a deployable frame adapted, in a contracted state, to be engaged in the left subclavian artery and adapted, in an expanded state, to press against the left subclavian artery;
   said aortic portion comprises a first opening created through said membrane, dimensioned so as to have an area at least equal, or less than, the transverse cross-section of said branch in the deployed state in the left subclavian artery; said aortic portion further comprises a second opening created through said membrane, arranged relative to said first opening, and dimensioned so as to be located substantially opposite the outlet of the brachiocephalic arteries and the left common carotid artery, when said first opening is located substantially opposite the outlet of the left subclavian artery;
   wherein:
   the center of said first opening is located on the axis of symmetry of a first V-shaped structure formed by said third annulus, the two segments of the first V-shaped structure diverging towards the proximal end of said aortic portion; the first opening is defined by an edge provided with a reinforcement which extends over the entire periphery of the first opening;
   said second opening comprises a proximal portion arranged above a second V-shaped structure formed by said second annulus, the two segments of the second structure diverging towards the proximal end of the aortic portion and being located on said axis of symmetry; lengthwise, said second opening extends between:
   a transverse proximal edge located at the distal bend formed by a third V-shaped structure, located on said axis of symmetry, of said first annulus;
   first lateral edges, diverging in the distal direction, which extend along the segments consecutive to the segments forming said second V-shaped structure;
   second lateral edges, converging in the distal direction, which extend along the segments of said first V-shaped structure; and
   the distal bend formed by said first V-shaped structure;
   said first to fourth annuli are consecutive to each other, or immediately consecutive to each other,
   said second opening being dimensioned so that it is located substantially opposite the outlets of the brachiocephalic and left common carotid arteries after placing the implant, and said second opening being configured not to receive any branch;
   the edges of the membrane which define said second opening being successively connected, from the proximal side and towards the distal side of the aortic portion, to the distal bend formed by said third V-shaped structure, to said segments consecutive to the segments forming said second V-shaped structure, to said segments forming said first V-shaped structure and to said distal bend formed by the first V-shaped structure.

2. The implant according to claim 1, wherein said reinforcement is radio-opaque and flexible, and in that said first opening is located near the distal bend of said first V-shaped structure formed by said third annulus.

3. The implant according to claim 1, wherein the distal bends of one of said first to third annuli are located at a distance of 0 to 10 mm from a plane transverse to the aortic portion passing through the proximal bends of the distally adjacent annulus.

4. The implant according to claim 1, wherein the diameter of said first to fourth annuli, in the deployed state, is greater than that of the membrane in the deployed state.

5. The implant according to claim 4, wherein the diameter of the annuli in the deployed state is 1 to 30% greater than that of the membrane in the deployed state.

6. The implant according to claim 1, wherein the end of said branch intended to be engaged through said first opening has, in the deployed state of said branch, a collar or a flared portion of diameter greater than that of said first opening, the collar or the flared portion thus being able to press against said aortic portion, on the inner side of the latter.

7. The implant according to claim 1, wherein the diameter of said first opening ranges from 5 to 11 mm.

8. The implant according to claim 1, wherein the dimension of said second opening in the longitudinal direction of said aortic portion ranges from 20 to 40 mm and in the circumferential direction of the aortic portion from 20 to 40 mm.

9. The implant according to claim 1, wherein said aortic portion comprises one or more radio-opaque markers located near said second opening, arranged so as to display the plane of the second opening on a medical imaging image.

10. An assembly formed by two stent-type aortic implants according to claim 1, the assembly comprising:
- a first implant in which a first edge of said first opening of said first implant turned towards a first adjacent edge of said second opening of said first implant is located at a distance from the adjacent edge ranging from 4 to 8 mm; and
- a second implant in which second edge of said first opening of said second implant turned towards a second adjacent edge of said second opening is located at a distance from said adjacent edge ranging from 8 to 12 mm.

11. The implant according to claim 4, wherein the diameter of the annuli in the deployed state is 20% greater than that of the membrane in the deployed state.

12. The implant according to claim 1, wherein the diameter of said first opening is equal to 8 mm.

13. An assembly formed by two stent-type aortic implants according to claim 1, the assembly comprising:
- a first implant in which a first edge of said first opening of said first implant turned towards a first adjacent edge of said second opening of said first implant is located at a distance from the adjacent edge equal to 5 mm; and
- a second implant in which a second edge of said first opening of said second implant turned towards a second adjacent edge of said second opening is located at a distance from said adjacent edge equal to 10.

* * * * *